(12) United States Patent
Charles, Jr. et al.

(10) Patent No.: US 7,799,568 B2
(45) Date of Patent: Sep. 21, 2010

(54) AUTHENTICATION OF PRODUCTS USING MOLECULARLY IMPRINTED POLYMERS

(75) Inventors: Harry K. Charles, Jr., Laurel, MD (US); George M. Murray, Columbia, MD (US)

(73) Assignee: The Johns Hopkins University, Baltimore, MD (US)

( * ) Notice: Subject to any disclaimer, the term of this patent is extended or adjusted under 35 U.S.C. 154(b) by 830 days.

(21) Appl. No.: 10/575,055

(22) PCT Filed: Oct. 4, 2004

(86) PCT No.: PCT/US2004/032576

§ 371 (c)(1),
(2), (4) Date: Apr. 13, 2007

(87) PCT Pub. No.: WO2005/038734

PCT Pub. Date: Apr. 28, 2005

(65) Prior Publication Data

US 2008/0056940 A1 Mar. 6, 2008

Related U.S. Application Data

(60) Provisional application No. 60/509,284, filed on Oct. 7, 2003.

(51) Int. Cl.
*G01N 31/22* (2006.01)
*G01N 21/64* (2006.01)
*G06K 19/06* (2006.01)
*G06K 19/14* (2006.01)
*B41M 3/14* (2006.01)
*B42D 15/10* (2006.01)
*B44F 1/12* (2006.01)

(52) U.S. Cl. .................. 436/56; 235/491; 283/72; 283/74; 283/79; 283/85; 283/92; 283/95; 427/7; 436/2; 436/5; 436/8; 436/85; 436/104; 436/172

(58) Field of Classification Search .............. 235/491; 283/72, 74, 79, 85, 91–92, 95; 427/7; 436/2, 436/5, 8, 56, 85, 172, 518, 531, 104
See application file for complete search history.

(56) References Cited

U.S. PATENT DOCUMENTS 4,374,120 A 2/1983 Soini et al.

(Continued)

OTHER PUBLICATIONS

Ueba, Y. et al, Journal of Applied Polymer Science 1980, 25, 2007-2017.*

(Continued)

*Primary Examiner*—Arlen Soderquist
(74) *Attorney, Agent, or Firm*—Francis A. Cooch

(57) ABSTRACT

A method for identifying a product includes providing a solid body (10) fabricated from at least a molecularly imprinted polymer having molecular sized cavities (12) adapted to selectively receive and bind molecules (50) having a specific taggant molecular structure (51), the molecular sized cavities (12) disposed on a portion of an exterior surface (11) of the body (10), and applying to the surface of the body a composition containing indicator molecules (50) having a taggant moiety (51) at one end and a marking function group (53) tethered to the taggant moiety (51) by a molecular chain the taggant moieties (51) engaging and binding to the molecular sized cavities (12) so as to mark the portion of the surface (11) of the body (10) with the indicator molecules (50) bound thereto, the marking functional groups (53) rendering the marked portion of the surface (11) perceptible with or without detection instrumentation.

30 Claims, 2 Drawing Sheets

U.S. PATENT DOCUMENTS

| | | | |
|---|---|---|---|
| 4,736,425 | A | 4/1988 | Jalon |
| 4,923,908 | A | 5/1990 | Lostumo |
| 5,005,873 | A | 4/1991 | West |
| 5,006,503 | A | 4/1991 | Byers et al. |
| 5,329,127 | A | 7/1994 | Becker et al. |
| 5,421,869 | A | 6/1995 | Gundjian et al. |
| 5,442,021 | A | 8/1995 | Heiliger |
| 5,587,273 | A | 12/1996 | Yan et al. |
| 5,696,240 | A | 12/1997 | Vallarino et al. |
| 5,728,296 | A | 3/1998 | Hjertén et al. |
| 5,814,223 | A | 9/1998 | Hjertén et al. |
| 5,916,445 | A | 6/1999 | Hjertén et al. |
| 5,942,444 | A | 8/1999 | Rittenburg et al. |
| 5,990,479 | A | 11/1999 | Weiss et al. |
| 6,458,599 | B1 | 10/2002 | Huang |
| 6,680,210 | B2 | 1/2004 | Huang |
| 6,692,031 | B2 | 2/2004 | McGrew |
| 2003/0129092 | A1 | 7/2003 | Murray |
| 2005/0241989 | A1* | 11/2005 | Sant et al. .................. 208/18 |

OTHER PUBLICATIONS

Williams, E. J. et al, Analytical Chemistry 1984, 56, 2523-2528.*

Meshkova, S. B. et al, Journal of Analytical Chemistry 2000, 55, 754-759.*

Jenkins, A. L. et al, "Polymer-Based Lanthanide Luminescent Sensor for Detection of the Hydrolysis Product of the Nerve Agent Soman in Water," Analytical Chemistry Jan. 15, 1999, vol. 71, No. 2, pp. 373-378.

Murray, G. M. et al, "Imprinted polymer sensors for contamination detection," proceedings of SPIE 2001 vol. 4206, pp. 131-139.

Sekine, T. et al, "Studies of the liquid-liquid partition systems. IV. Solvent extraction study of europium (III) adduct chelate complexes with six acetylacetone derivatives and tributyl phosphate" Bulletin of the Chemical Society of Japan, Dec. 1965, vol. 38, No. 12, pp. 2087-2094.

* cited by examiner

AUTHENTICATION OF PRODUCTS USING MOLECULARLY IMPRINTED POLYMERS

CROSS-REFERENCE TO RELATED APPLICATIONS

This application claims the benefit of prior filed co-pending U.S. Provisional Application No. 60/509,284, filed Oct. 7, 2003, the contents of which are incorporated herein by reference.

BACKGROUND OF THE INVENTION

1. Field of the Invention

The present invention generally relates to a method of marking a product to identify its origin or contents based on information such as, for example, date of manufacture, plant of origin, etc.

2. Description of the Related Art

Major problems experienced in many areas of the world and in connection with many different products is that of product counterfeiting, unauthorized distribution and sale of a product (e.g. grey market trading, parallel trading, product diversion), as well as false liability based on product substitution.

Throughout the world, manufacturers provide the products they sell with a visually distinctive appearance, packaging or labels so that customers can distinguish their products from those of others. As a result, their customers learn to associate the visually distinctive appearance with certain standards of quality. If the customers are satisfied with those standards, they will buy products provided with that visually distinctive appearance in preference to others. Once customers have acquired a preference for products provided with a particular visually distinctive appearance, the manufacturers become vulnerable to product counterfeiting.

A counterfeit product consists of a product that is provided with a visually distinctive appearance, or a brand name, confusingly similar to that of a genuine product. Customers seeing the visually distinctive appearance or the familiar brand name provided to the counterfeit product, buy this product in the expectation that they are buying a genuine product.

There are many ways known of providing products with a visually distinctive appearance. In general, the visually distinctive appearance is provided either directly to the product or to an article with which the material is associated such as, for example, a label, wrapper or container. The visually distinctive appearance may be, for example, a distinctive shape or configuration, a distinctive marking, or a trademark. The material of a counterfeit product may be the same as, or different from the material of a genuine product. Often the material of the counterfeit product is the same, but of inferior quality. For instance, it is usually difficult to distinguish a chemical product having a particular chemical formula and made by one manufacturer, from the same chemical, with the same formula, but made by a different manufacturer. This is particularly so if the two manufacturers use the same production process. For this reason, it is not difficult for the unscrupulous to establish the chemical formula of an active ingredient in a composition, and the relative amounts of the various ingredients in the composition, and then pass off his own product as that of another manufacturer.

Accordingly, there is a need for methods for marking products to authenticate ownership thereof. Thus, a counterfeit and a genuine product can be distinguished by the absence of the marker in the former and the presence of the marker in the latter.

SUMMARY OF THE INVENTION

In accordance with one embodiment of the present invention, a method for identifying a product is provided comprising (a) providing a solid body fabricated from at least a molecularly imprinted polymer having molecular sized cavities adapted to selectively receive and bind molecules having a specific taggant molecular structure, said molecular sized cavities being disposed on at least a selected portion of an exterior surface of the body; (b) applying to the surface of the body a composition containing indicator molecules having a taggant moiety at one end having the taggant molecular structure and a marking functional group tethered to the taggant moiety by a molecular chain, the taggant moieties engaging and binding to the molecular sized cavities so as to mark the selected portion of the surface of the body with the indicator molecules bound thereto, said marking functional groups rendering the marked portion of the surface perceptible with or without detection instrumentation.

In accordance with a second embodiment of the present invention, a product identification system comprising:

a) a package body fabricated from at least a molecularly imprinted polymer having molecular sized cavities adapted to selectively receive and bind molecules having a specific taggant molecular structure, said molecular sized cavities being disposed on selected portions of an exterior surface of the body, said selected portions being configured in the form of information conveying indicia; and, b) a developing composition for developing the selected portions as an image, said developing composition including indicator molecules having a taggant moiety at one end having the taggant molecular structure and a marking functional group tethered to the taggant moiety by a molecular chain, said taggant moieties engaging and binding to the molecular sized cavities so as to mark the portion of the surface of the body with the indicator molecules bound thereto, said marking functional groups rendering the marked portion of the surface perceptible with or without detection instrumentation.

BRIEF DESCRIPTION OF THE DRAWINGS

Various embodiments are described below with reference to the drawings wherein.

DETAILED DESCRIPTION OF PREFERRED EMBODIMENT(S)

Figure 1:
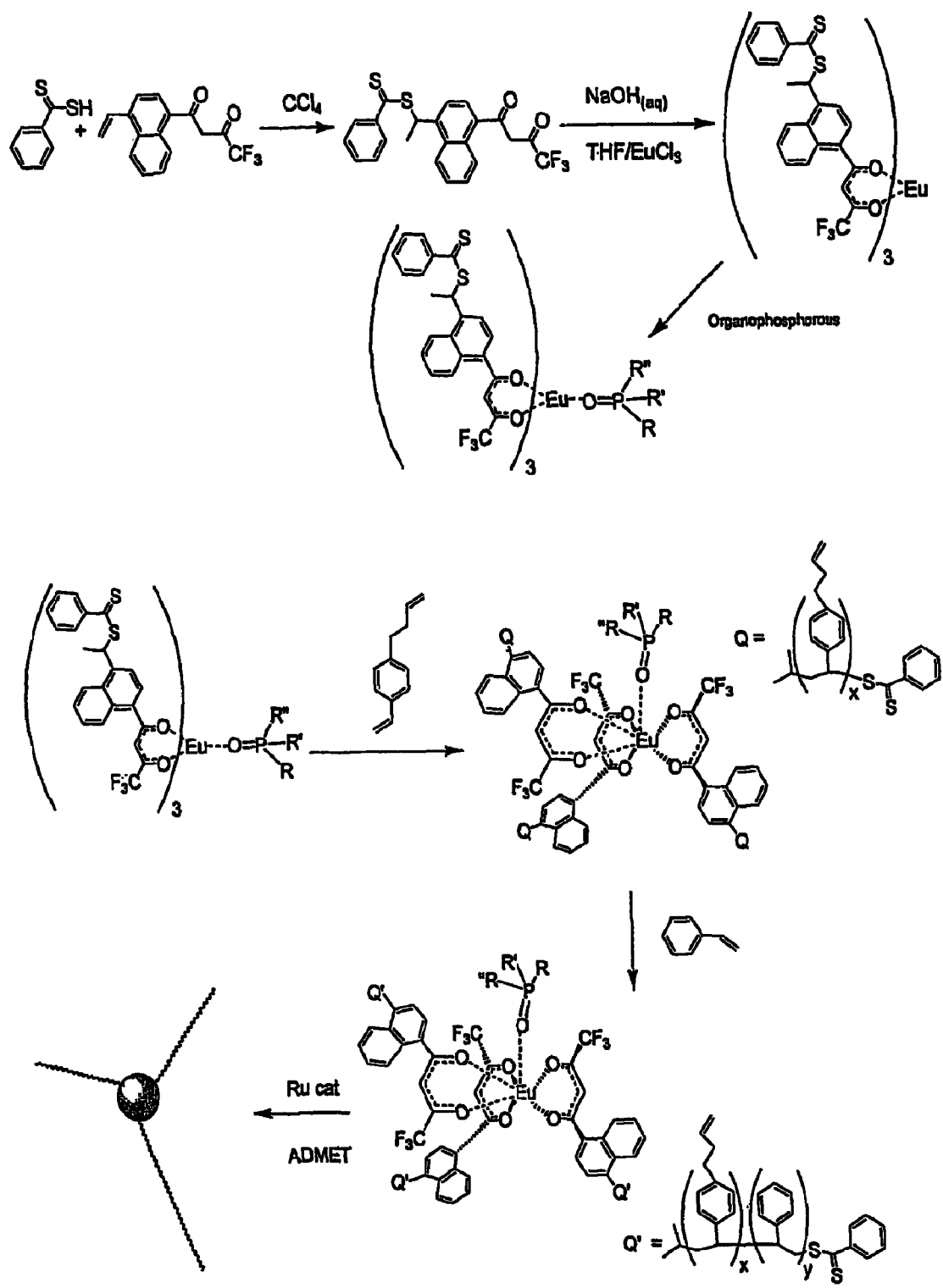
FIG. 1 is a schematic flow chart illustrating the synthesis procedures for an embodiment of a molecularly imprinted polymer of the present invention; and, FIGS. 2 to 6 illustrate a method for marking a body for identification in accordance with the invention.
Figure 2:
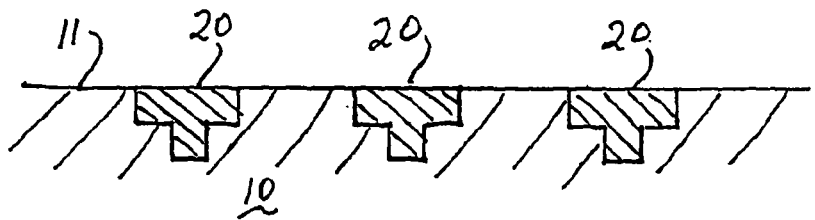

The present invention is directed to a method of authenticating the origin or commercial source or supplier of a product. The method advantageously employs a molecularly imprinted polymer ("MIP") and provides a simple means of authentication which is difficult to overcome by counterfeiters. The method is particularly well adapted to injection molded epoxy based electronics packages.

Molecularly imprinted polymers (MIPs) are made by first building a complex of a target molecule and associated attached binding molecules that possess the ability to be incorporated into a polymer. The complex is usually dissolved in a larger amount of other polymerizable molecules. The bulk of the other molecules of the polymer are made with crosslinking monomers. These molecules have two places to bind to the polymer chain to form a rigid three-dimensional structure. The crosslinkers are necessary to hold the complexing molecules in place after the target molecule (also called a "template," "analyte" or "taggant") is removed. Typically, after polymerization, a chunk of plastic is obtained.

The method of the present invention can be performed with any polymer suitable for the purposes described herein, although epoxies are especially preferred. Epoxies form highly crosslinked polymers. By adding an innocuous "taggant" molecule to the epoxy it will be incorporated into the resin from which the package is made. The taggant is subsequently removed from the entire surface or, preferably, a portion of the surface of the package body, for example, by leaching out with an appropriate solvent. The polymer is left with special molecular sized cavities configured to selectively receive the target molecule, somewhat analogous to a lock and key. The cavities recapture the target molecule and also provide a binding site for larger molecules that have the molecular configuration of the target as part of their structure. The cavities are invisible to normal methods of surface imaging and would be incomprehensible to atomic force microscopy due to the random nature of the cavity sites, thus rendering the taggant difficult if not impossible to reverse engineer.

Authentication is provided in the following method manner. A developer fluid containing a chemical indicator is applied to the product (i.e., package). The indicator includes a molecule having the taggant moiety at one end which is tethered to a chromophore or other marking functional group by means of a molecular chain, such as a long alkyl chain. The taggant end of the molecule engages the corresponding molecular cavities like a key fitting into a lock and is held there, thereby binding the indicator molecule to the surface of the package. The excess indicator fluid is then washed off. Any package not having molecular cavities corresponding to the specific taggant will not bind the indicator molecules. Thus, indicator molecules remaining bound to the surface of the package after the washing are proof that the package is identified with the taggant. The chromophore functionality can be chosen so as to luminesce when excited by light of a specific wavelength. For example, a light emitting diode or lamp of the appropriate wavelength can be used to illuminate the package and the resulting luminescence would indicate the presence of the chromophore, thereby identifying the package.

Various types of information can be encoded into the package such as, for example, the date of manufacture, plant of origin, contents of package, etc. By removing the taggants from only specific portions of the of the package messages can be encoded. The indicator molecules will bind only to the available areas where the taggants have been removed and permit the visualization of the message as, for example, a luminescent or colored message.

An MIP useful for incorporating a taggant molecule into a resin body is described in U.S. patent application Ser. No. 10/359,322, filed Feb. 6, 2003, which is herein incorporated by reference in its entirety.

Yet another preferred procedure for making the MIP is by RAFT polymerization. RAFT polymerization is described in U.S. Pat. Nos. 6,747,111, 6,737,488, 6,642,318 and 6,458,968, and in foreign publication WO 98/01478, all of which are incorporated by reference. In one embodiment of the present invention, a RAFT star polymerization method for making a star MIP comprises the steps:

(a) providing a complex comprising a compound of the general formula $L_3M$ wherein L is the same or different and is a β-diketone ligand containing the same or different chain transfer moiety and M is a lanthanide element;

(b) reacting the complex of step (a) with a target analyte to provide an adduct containing the target analyte;

(c) co-polymerizing the adduct of step (b) with a monomer and optional cross-linking agent to provide a polymer; and (d) removing the target analyte from the polymer to provide the MIP.

The lanthanide elements, also known as the rare earth elements, consist of the elements having atomic numbers from 57 to 71. As used herein, the term "lanthanide" refers to the following elements of the periodic table: lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), and lutetium (Lu). In the present invention, a lanthanide is chosen as the transducer because the trivalent lanthanide ions have excellent spectroscopic properties such as long luminescence lifetimes and narrow bandwidths, usually only a few nanometers. Preferred lanthanide ions that exhibit a narrow-line luminescence include the +3 ions of samarium, europium, dysprosium, terbium, and neodymium, with europium being most preferred.

Providing the Lanthanide Complex

The ligand L of the lanthanide complex is a β-diketone generally having the structure:

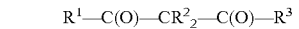

$$R^1—C(O)—CR^2_2—C(O)—R^3$$

wherein $R^1$ is a hydrocarbon group having 1 to about 20 carbons and containing a chain transfer moiety; $R^2$ can be the same or different and is hydrogen or a hydrocarbon group having from 1 to about 12 carbon atoms and $R^3$ is a straight or branched chain alkyl group of 1 to about 12 carbon atoms optionally containing one or more halogen atoms.

In one embodiment, the hydrocarbon group of $R^1$ is a substituted or unsubstituted alkyl group; a cycloalkyl group; a substituted or unsubstituted aryl group, e.g., a phenyl group, a naphthyl group and the like; a substituted or unsubstituted alkaryl group, e.g., 2-methylphenyl group (o-tolyl group), 3-methylphenyl group (m-tolyl group), 4-methylphenyl group (p-tolyl group), 2,3-dimethylphenyl group (2,3-xylyl group), 3,4-dimethylphenyl group (3,4-xylyl group), 2,4,6-trimethylphenyl group (mesityl group) and the like; a substituted or unsubstituted aralkyl group, e.g., phenylmethyl group (benzyl group), phenylethyl group (phenethyl group), triphenylmethyl group (trityl group) and the like; a substituted or unsubstituted monocyclic aromatic group, e.g., benzene, methylbenzene (toluene), 1,2-dimethylbenzene (o-xylene), 1,3-dimethylbenzene (m-xylene), 1,4-dimethylbenzene (p-xylene), 1,3,5-trimethylbenzene (mesitylene), 1,2,3-trimethylbenzene, 1,2,4-trimethylbenzene, tetramethylbenzene, pentamethylbenzene, ethylbenzene, n-propylbenzene, isopropylbenzene (cumene), 1-isopropyl-4-methylbenzene (p—Cymene), n-butylbenzene, 2-butylbenzene, isobutylbenzene, tert-butylbenzene, n-pentylbenzene, cyclopentylbenzene, neopentylbenzene, cyclohexylbenzene, 1—Cyclohexyl-4-methylbenzene, cyclooctylbenzene and the like; or a substituted or unsubstituted polycyclic aromatic hydrocarbon group, e.g., biphenyl, biphenylene, terphenyl, naphthalene, azulene, anthracene, phenanthrene, triphenylene, pyrene, 1-methylnaphthalene, 2-methylnaphthalene, 1-ethylnaphthalene, 2-ethylnaphthalene, 2,21-dimethylbiphenyl, diphenylethane, 1,2-diphenylethane, 1,8-diphenyloctane and the like.

Useful chain transfer moieties include, but are not limited to, dithiocarboxylic ester groups (—S—C(S)R) wherein R is a hydrocarbon group having from 1 to about 20 carbon atoms, including by way of example, straight or branched aliphatic, cycloaliphatic and aromatic groups and cycloaliphatic and aromatic groups substituted with one or more straight or branched aliphatic, cycloaliphatic and/or aromatic groups; trithiocarbamates; benzyl iodides; hydroxyl groups (—OH), ketone groups, alkoxy groups (—OR), carboxyl groups (—COOH), ester groups (—COOR), aldehyde group (—CHO), acyl groups (—C(O)R), amide groups (—C(O)NH$_2$), substituted amide groups (—C(O)NHR), —C(O)NR$_2$), amino groups (—NH$_2$), substituted amino groups (—NHR, —NR$_2$), nitro groups (—NO$_2$), nitroso groups (—NO), unsubstituted and substituted cyano groups (—CN), cyanate groups (—OCN), isocyanate groups (—NCO), thiocyanate groups (—SCN), isothiocyanate group (—NCS), thiol group (—SH), and the like.

In another embodiment of the present invention, one $R^2$ is hydrogen and the other $R^2$ is an alkyl of 1 to 6 carbon atoms. In another embodiment, $R^3$ is an alkyl halide group of the formula (—$R^4$)$_t$CX$_3$) wherein $R^4$ is a hydrocarbon group of 1 to about 12 carbon atoms, t is 0 or 1 and X is a halide, e.g., Cl, F, Br, I with F being preferred. In another embodiment, $R^3$ is the same as $R^1$.

In a preferred embodiment of the present invention, ligand L is a fluorinated, β-diketone having the structure:

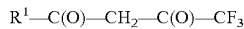

wherein $R^1$ is a hydrocarbon group having from 1 to about 20 carbon atoms and includes a chain transfer moiety. The chain transfer moiety preferably includes a dithiocarboxylic ester (e.g., RC(S)—S—) functionality wherein R has the aforestated meaning; a trithiocarbonates and/or a benzyl iodide. Preferably, $R^1$ is an aromatic groups such as benzene and/or naphthalene groups.

In general, the complex can be formed by reacting about three moles of ligand (the same ligand or mixedligands) with about one mole of lanthanide halide such as EuCl$_3$. This reaction is generally carried out in an aqueous solution in the presence of an alkali hydroxide (e.g., NaOH). The ligand is preferably first dissolved in a solvent such as tetrahydrofuran (THF), and the reaction is terminated by the addition of an alcohol (e.g., methanol). The precipitated complex is extracted by filtration with further purification.

Reacting the Lanthanide Complex with the Analyte

The reaction of the lanthanide complex with the target analyte (e.g., an organophosphorus compound) can be carried out by first dissolving the target analyte in a suitable solvent and then reacting it with the complex at a temperature of from ambient to about 100° C. for a sufficient period of time (e.g., about 1 to about 10 hours). If desired, the reaction can be conducted under an inert atmosphere (e.g., in nitrogen, argon, etc.). The resulting adduct can then be separated by known techniques. A preferred target organophosphorus analyte is a compound having the formula ($R^5$)($R^6$)($R^7$)P=O, wherein $R^5$, $R^6$ and $R^7$ can be the same or different and are individually selected from inorganic or organic groups, provided that at least one group is organic. Exemplary groups include, but are not limited to, those selected from H, —OH, halogen (e.g., F, Cl, Br, I), nitrile (—CN), nitro (NO$_2$), and organic groups such as, for example, substituted or unsubstituted aliphatic or aromatic groups with or without heteroatoms such as, for example, alkyl, cycloalkyl, alkenyl, alkoxy, and the like. The organophosphorus compound is exemplified herein with the use of dimethyl hydrogen phosphate [(CH$_3$O)$_2$P(O)H], or pinacolyl methyl phosphonate ("PMP") having the formula:

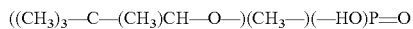

Polymerization

The MIP is prepared by RAFT polymerization of a monomer using the L$_3$M-target analyte adduct.

A wide variety of monomers may be used for synthesizing the MIP in accordance with the principles of the present invention. Suitable non-limiting examples of monomers that can be used for preparing a MIP of the present invention include methylmethacrylate, other alkyl methacrylates, alkylacrylates, allyl or aryl acrylates and methacrylates, cyanoacrylate, styrene, -methyl styrene, vinyl esters, including vinyl acetate, vinyl chloride, methyl vinyl ketone, vinylidene chloride, acrylamide, methacrylamide, acrylonitrile, methacrylonitrile, 2-acetamido acrylic acid; 2-(acetoxyacetoxy)ethyl methacrylate 1-acetoxy-1,3-butadiene; 2-acetoxy-3-butenenitrile; 4-acetoxystyrene; acrolein; acrolein diethyl acetal; acrolein dimethyl acetal; acrylamide; 2-acrylamidoglycolic acid; 2-acrylamido-2-methyl propane sulfonic acid; acrylic acid; acrylic anhydride; acrylonitrile; acryloyl chloride; (R)-acryloxy-'-dimethyl-g-butyrolactone; N-acryloxy succinimide-acryloxytris(hydroxymethyl) aminomethane; N-acryloly chloride; N-acryloyl pyrrolidinone; N-acryloyl-tris(hydroxymethyl)amino methane; 2-amino ethyl methacrylate; N-(3-aminopropyl)methacrylamide; (o, m, or p)-amino-styrene; t-amyl methacrylate; 2-(1-aziridinyl) ethyl methacrylate; 4-benzyloxy-3-methoxystyrene; 2-bromoacrylic acid; 4-bromo-1-butene; 3-bromo-3,3-difluoropropane; 6-bromo-1-hexene; 3-bromo-2-methacrylonitrile; 2-(bromomethyl)acrylic acid; 8-bromo-1-octene; 5-bromo-1-pentene; cis-1-bromo-1-propene; -bromostyrene; p-bromostyrene; bromotrifluoro ethylene; (±)-3-buten-2-ol; 1,3-butadiene; 1,3-butadiene-1,4-dicarboxylic acid 3-butenal diethyl acetal; 1-butene; 3-buten-2-ol; 3-butenyl chloroformate; 2-butylacrolein; -t-butylacrylamide; butyl acrylate; butyl methacrylate; (o,m,p)-bromostyrene; t-butyl acrylate; (R)-carvone; (S)-carvone; (—)-carvyl acetate; cis 3-chloroacrylic acid; 2-chloroacrylonitrile; 2-chloroethyl vinyl ether; 2-chloromethyl-3-trimethylsilyl-1-propene; 3-chloro-1-butene; 3-chloro-2-chloromethyl-1-propene; 3-chloro-2-methyl propene; 2,2-bis(4-chlorophenyl)-1,1-dichloroethylene; 3-chloro-1-phenyl-1-propene; m-chlorostyrene; o-chlorostyrene; p-chlorostyrene; 1-cyanovinyl acetate; 1-cyclopropyl-1-(trimethylsiloxy)ethylene; 2,3-dichloro-1-propene; 2,6-dichlorostyrene; 1,3-dichloropropene; 2,4-diethyl-2,6-heptadienal; 1,9-decadiene; 1-decene; 1,2-dibromoethylene; 1,1-dichloro-2,2-difluoroethylene; 1,1-dichloropropene; 2,6-difluorostyrene; dihydrocarveol; (±)-dihydrocarvone; (−)-dihydrocarvyl acetate; 3,3-dimethylacrylaldehyde; N,N'-dimethylacrylamide; 3,3-dimnethylacrylic acid; 3,3-dimethylacryloyl chloride; 2,3-dimethyl-1-butene; 3,3-dimethyl-1-butene; 2-dimethyl aminoethyl methacrylate; 1-(3-butenyl)-4-vinylbenzene; 2,4-dimethyl-2,6-heptadien-1-ol; 2,4-dimethyl-2,6-heptadienal; 2,5-dimethyl-1,5-hexadiene; 2,4-dimethyl-1,3-pentadiene; 2,2-dimethyl-4-pentenal; 2,4-dinethylstyrene; 2,5-dimnethylstyrene; 3,4-dimethylstryene; 1-dodecene; 3,4-epoxy-1-butene; 2-ethyl acrolein; ethyl acrylate; 2-ethyl-1-butene; (±)-2-ethylhexyl acrylate; (±)-2-ethylhexyl methacrylate; 2-ethyl-2-(hydroxymethyl)-1,3-propanediol triacrylate; 2-ethyl-2-(hydroxymethyl)-1,3-propanediol trimethacrylate; ethyl methacrylate; ethyl vinyl ether; ethyl vinyl ketone; ethyl vinyl sulfone; (1-ethylvinyl)tributyl tin; m-fluorostyrene; o-fluorostyrene; p-fluorostyrene; glycol methacrylate (hydroxyethyl methacrylate); GA GMA; 1,6-heptadiene; 1,6-heptadienoic acid; 1,6-heptadien-4-ol; 1-heptene; 1-hexen-3-ol; 1-hexene; hexafluoropropene; 1,6-hexanediol diacrylate; 1-hexadecene; 1,5-hexadien-3,4-diol; 1,4-hexadiene; 1,5-hexadiem-3-ol; 1,3,5-hexatriene; 5-hexen-1,2-diol; 5-hexen-1-ol; hydroxypropyl acrylate; 3-hydroxy-3,7,11-trimethyl-1,6,10-dodecatriene; isoamyl methacrylate; isobutyl methacrylate; isoprene; 2-isopropenylaniline; isopropenyl chloroformate; 4,4'-isopropylidene dimethacrylate; 3-isopropyl-a-a-dimethylbenzene isocyanate; isopulegol; itaconic acid; itaconalyl chloride; (±)-:linalool; linalyl acetate; p-mentha-1,8-diene; p-mentha-6,8-dien-2-ol; methyleneamino acetonitrile; methacrolein; [3-(methacryloylamino)-propyl] trimethylammonium chloride; methacrylamide; methacrylic acid; methacrylic anhydride; methacrylonitrile; methacryloyl chloride; 2-(methacryloyloxy)ethyl acetoacetate; (3-methacryloxypropyl) trimethoxy silane; 2-(methacryloxy)ethyl trimethyl ammonium methylsulfate; 2-methoxy propene (isopropenyl methyl ether); methyl-2-(bromomethyl)acrylate; 5-methyl-5-hexen-2-one; methyl methacrylate; N,N'-methylene bisacrylamide; 2-methylene glutaronitrile; 2-methylene-1,3-propanediol; 3-methyl-1,2-butadiene; 2-methyl-1-butene; 3-methyl-1-butene; 3-methyl-1-buten-1-ol; 2-methyl-1-buten-3-yne; 2-methyl-1,5-heptadiene; 2-methyl-1-heptene; 2-methyl-1-hexene; 3-methyl-1,3-pentadiene; 2-methyl-1,4-pentadiene; (±)-3-methyl-1-pentene; (±) 4-methyl-1-pentene; (±)-3-methyl-1-penten-3-ol; 2-methyl-1-pentene; —methyl styrene; t-methylstyrene; t-methylstyrene; 3-methylstyrene; methyl vinyl ether; methyl vinyl ketone; methyl-2-vinyloxirane; 4-methylstyrene; methyl vinyl sulfone; 4-methyl-5-vinylthiazole; myrcene; t-Nitrostyrene; 3-Nitrostyrene; 1-Nonadecene; 1,8-nonadiene; 1-octadecene; 1,7-octadiene; 7-octene-1,2-diol; 1-octene; 1-octen-3-ol; 1-pentadecene; 1-pentene; 1-penten-3-ol; t-2,4-pentenoic acid; 1,3-pentadiene; 1,4-pentadiene; 1,4-pentadien-3-ol; 4-penten-1-ol; 4-penten-2-ol; 4-phenyl-1-butene; phenyl vinyl sulfide; phenyl vinyl sulfonate; 2-propene-1-sulfonic acid sodium salt; phenyl vinyl sulfoxide; 1-phenyl-1-(trimethylsiloxy)ethylene; propene; safrole; styrene (vinyl benzene); 4-styrene sulfonic acid sodium salt; styrene sulfonyl chloride; 3-sulfopropyl acrylate potassium salt; 3-sulfopropyl methacrylate sodium salt; tetrachloroethylene; tetracyano ethylene; trans 3-chloroacrylic acid; 2-trifluoromethyl propene; 2-(trifluoromethyl)propenoic acid; 2,4,4'-trimethyl-1-pentene; 3,5-bis(trifluoromethyl)styrene; 2,3-bis(trimethylsiloxy)-1,3-butadiene; 1-undecene; vinyl acetate; vinyl acetic acid; 4-vinyl anisole; 9-vinyl anthracene; vinyl behenate; vinyl benzoate; vinyl benzyl acetate; vinyl benzyl alcohol; 3-vinyl benzyl chloride; 3-(vinyl benzyl)-2-chloroethyl sulfone; 4-(vinyl benzyl)-2-chloroethyl sulfone; N-p-vinyl benzyl)-N,N'-dimethyl amine; 4-vinyl biphenyl (4-phenyl styrene); vinyl bromide; 2-vinyl butane; vinyl butyl ether; 9-vinyl carbazole; vinyl carbinol; vinyl cetyl ether; vinyl chloroacetate; vinyl chloroformate; vinyl crotanoate; vinyl cyclohexane; 4-vinyl-1-cyclohexene; 4-vinylcyclohexene dioxide; vinyl cyclopentene; vinyl dimethylchlorosilane; vinyl dimethylethoxysilane; vinyl diphenylphosphine; vinyl 2-ethyl hexanoate; vinyl 2-ethylhexyl ether; vinyl ether ketone; vinyl ethylene; vinyl ethylene iron tricarbonyl; vinyl ferrocene; vinyl formate; vinyl hexadecyl ether; vinylidene fluoride; 1-vinyl imidizole; vinyl iodide; vinyl laurate; vinyl magnesium bromide; vinyl mesitylene; vinyl 2-methoxy ethyl ether; vinyl methyl dichlorosilane; vinyl methyl ether; vinyl methyl ketone; 2-vinyl naphthalene; 5-vinyl-2-norbomene; vinyl pelargonate; vinyl phenyl acetate; vinyl phosphonic acid, bis(2-chloroethyl)ester; vinyl propionate; 4-vinyl pyridine; 2-vinyl pyridine; 1-vinyl-2-pyrrolidinone; 2-vinyl quinoline; 1-vinyl silatrane; vinyl sulfone; vinyl sulfonic acid sodium salt; o-vinyl toluene; p-vinyl toluene; vinyl triacetoxysilane; vinyl tributyl tin; vinyl trichloride; vinyl trichlorosilane; vinyl trichlorosilane (trichlorovinylsilane); vinyl triethoxysilane; vinyl triethylsilane; vinyl trifluoroacetate; vinyl trimethoxy silane; vinyl trimethyl nonylether; vinyl trimethyl silane; vinyl triphenyphosphonium bromide (triphenyl vinyl phosphonium bromide); vinyl tris-(2-methoxyethoxy) silane; vinyl 2-valerate and the like and mixtures thereof.

Acrylate-terminated or otherwise unsaturated urethanes, carbonates, and epoxies can also be used in the MIP. An example of an unsaturated carbonate is allyl diglycol carbonate. Unsaturated epoxies include, but are not limited to, glycidyl acrylate, glycidyl methacrylate, allyl glycidyl ether, and 1,2-epoxy-3-allyl propane.

Crosslinking agents that impart rigidity or structural integrity to the MIP are known to those skilled in the art, and include di-, tri- and tetrafuctional acrylates or methacrylates, divinylbenzene (DVVB), alkylene glycol and polyalkylene glycol diacrylates and methacrylates, including ethylene glycol dimethacrylate (GDMA) and ethylene glycol diacrylate, vinyl or allyl acrylates or methacrylates, divinylbenzene, diallyldiglycol dicarbonate, diallyl maleate, diallyl fumarate, diallyl itaconate, vinyl esters such as divinyl oxalate, divinyl malonate, diallyl succinate, triallyl isocyanurate, the dimethacrylates or diacrylates of bis-phenol A or ethoxylated bis-phenol A, methylene or polymethylene bisacrylamide or bismethacrylamide, including hexamethylene bisacrylamide or hexamethylene bismethacrylamide, di(alkene) tertiary amines, trimethylol propane triacrylate, pentaerytiritol tetraacrylate, divinyl ether, divinyl sulfone, diallyl phthalate, triallyl melamine, 2-isocyanatoethyl methacrylate, 2-isocyanatoethylacrylate, 3-isocyanatopropylacrylate, 1-methy:L-2-isocyanatoethyl methacrylate, 1,1-dimnethyl-2-isocyanaotoethyl acrylate, tetraethylene glycol diacrylate, tetraethylene glycol dimethacrylate, triethylene glycol diacrylate, triethylene glycol dimethacrylate, hexanediol dimethacrylate, hexanediol diacrylate, divinyl benzene; 1,3-divinyltetramethyl disiloxane; 8,13-divinyl-3,7,12,17-tetramethyl-21H,23H-porphine; 8,13-divinyl-3,7,12,17-tetramethyl-21H,23H-propionic acid; 8,13-divinyl-3,7,12,17-tetramethyl-21H,23H-propionic acid disodium salt; 3,9-divinyl-2,4,8,10-tetraoraspiro[5,5]undecane; divinyl tin dichloride and the like.

The polymerization can be carried out neat or in a porogen, or solvent, which can be any solvent suitable for the purposes described herein. Suitable solvents include, but are not limited to, toluene, xylene, methoxyethanol, and the like and mixtures.

Any suitable conditions effective to polymerize the monomers of the present invention to produce an MIP without dissociating the chelated lanthanide-analyte complex may be used. The monomers of the present invention may be polymerized by free radical polymerization, and the like.

Any UV or thermal free radical initiator known to those skilled in the art can be used in the free radical polymerization. Examples of UV and thermal initiators include benzoyl peroxide, acetyl peroxide, lauryl peroxide, azobisisobutyronitrile (AIBN), t-butyl peracetate, cumyl peroxide, t-butyl peroxide; t-butyl hydroperoxide, bis(isopropyl)peroxy-dicarbonate, benzoin methyl ether, 2,2'-azobis(2,4-dimethylvaleronitrile), tertiarybutyl peroctoate, phthalic peroxide, diethoxyacetophenone, and tertiarybutyl peroxypivalate, diethoxyacetophenone, 1-hydroxycyclohexyl phenyl ketone, 2,2-dimethyoxy-2-phenylacetophenone, and phenothiazine, diisopropylxanthogen disulfide, 2,2'-azobis-(2-amidinopropane); 2,2'-azobisisobutyronitrile-; 4,4'-azobis-(4-cyanovaleric acid); 1,1'-azobis-(cyclohexanecarbonitrile)-; 2,2'-azobis-(2,4-dimethylvaleronitrile); and the like and mixtures thereof.

The choice of monomer and cross-linking agent will be dictated by the chemical (hydrophilicity, chemical stability, degree of cross-linking, ability to graft to other surfaces, interactions with other molecules, etc.) and physical (porosity, morphology, mechanical stability, etc.) properties desired for the polymer. The amounts of chelated lanthanide-analyte complex, monomer and crosslinking agents should be chosen to provide a crosslinked polymer exhibiting the desired structural integrity, porosity and hydrophilicity. The amounts can vary broadly, depending on the specific nature/reactivities of the chelated lanthanide-analyte complex, monomer and crosslinking agent chosen as well as the specific application and environment in which the polymer will ultimately be employed. The relative amounts of each reactant can be varied to achieve desired concentrations of chelated lanthanide-analyte complexes in the polymer support structure. Typically, the amount of chelated lanthanide-analyte complex will be on the order of about 0.01 mmol to about 100 mmol percent of monomer. The solvent, temperature, and means of polymerization can be varied in order to obtain polymeric materials of optimal physical or chemical features, for example, porosity, stability, and hydrophilicity. The solvent will also be chosen based on its ability to solubilize all the various components of the reaction mixture.

Polymerizations are generally conducted in bulk solution by the free-radical method. For bulk polymerization, typically the amount of chelated lanthanide-analyte complex will be on the order of about 0.01 mmol to about 100 mmol percent of monomer, about 90 to about 99 mol percent monomer and about 1.0 to about 10 mol percent cross-linker, and about 1 mol percent of a free radical initiator are dissolved in an aqueous/organic two-phase solvent. The reaction mixture is placed under an inert atmosphere and heated to a temperature of from about 50° C. to about 100° C. for about 24 to about 72 hours. As one skilled in the art will readily appreciate, styrenic polymerizations can be thermally initiated. It is particularly advantageous to prepare a block copolymer employing two or more of the foregoing monomers (See FIG. 1).

When polymerization is complete, the crosslinked polymer may be washed, cryogenically ground to a uniformly fine powder, and/or extensively eluted with nonpolar solvents to remove any unreacted lanthanide-analyte complex. The steps of grinding and/or freezing in liquid nitrogen may be used to maximize surface area and allow for access by the various reagents and samples. Freezing allows the polymer to become brittle enough to be ground and prevents distortions of the polymer by the heat of friction. The MIPs can be used in the construction of solid bodies used, for example, as packages for electronic components.

Removal of the target molecule leaves a macroporous polymer with complementary molecular cavities which include lanthanide complexes that have specific binding affinity for the target molecule. See FIG. 1. The target molecule comprising, for example, an organophosphorus compound, may be dissociated from the metal ion complex binding site within the polymer in a manner that does not adversely affect the imprinted cavity. In embodiments wherein the target molecule is covalently bound to the functional monomer, any appropriate method can be used to cleave the covalent bond, although the covalent bond formed should preferably be cleaved under conditions suitable to release the imprint molecule after the MIP is formed, without adversely affecting the selective binding characteristics of the MIP. To accomplish this, acetone, isopropanol, methanol or other suitable organic solvent may be used to swell the resultant polymers, allowing greater access to the coordinated metal ions because imprinted resins have a relatively low amount of functionalization and are primarily nonionic matrices. The covalent bond that is cleaved to release the imprint molecule can optionally provide an additional polar or ionic site for design and imprinting of the imprint molecule. In preferred embodiments wherein the target analyte is associated with the lanthanide in a non-covalent manner, the non-covalently bound analyte is simply leached or washed out after polymerization. For example, for organophosphorus compound imprinted resins, subsequent to the removal of unreacted monomer, a 1 N aqueous acidic solution may be mixed into the acetone washes, with increasing aqueous acidic phase in each sequential wash, to remove the imprint molecule from the cavities. In certain preferred embodiments, an acidic solvent having a pH of about 4.5 or less is used. In certain other preferred embodiments, resin mass action is used to replace a target anion with an easily exchangeable anion by immersing the polymer in a solution containing the easily exchangeable anion at a suitable pH.

Figure 3:
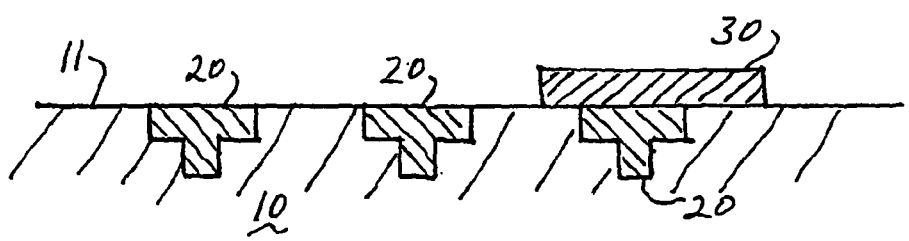
Figure 4:
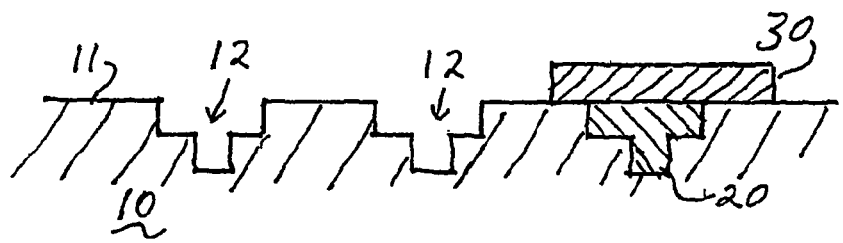

Referring now to FIGS. 2 to 6, a body 10 is fabricated from a MIP having taggant molecules 20 incorporated into the surface 11 of the body. In one embodiment of the invention a mask 30 is deposited on the surface 11 (as shown in FIG. 3) in accordance with known masking methods. The masking material is selected so as to resist solvents used for leaching the taggants. The mask can be deposited in any configuration. For example, the mask configuration can leave selected unmasked portions of the surface configured in the form of indicia employed to convey information, such as a bar code or other symbol, code, alphanumeric indicia, etc. The protected area covered by the mask 30 includes complexed taggants which will not be removed in the subsequent leaching step. Referring to FIG. 4, the surface 11 of the body 10 is treated with a solvent to leach out the taggant molecules from the unmasked area leaving molecular sized cavities 12 adapted to selectively receive the indicator molecules.

In embodiments wherein the imprint or taggant molecule is covalently bound to the functional monomer, any appropriate method can be used to cleave the covalent bond, although the covalent bond formed should preferably be cleaved under conditions suitable to release the imprint molecule after the MIP is formed, without adversely affecting the selective binding characteristics of the MIP. To accomplish this, acetone, isopropanol, methanol or other suitable organic solvent may be used to swell the resultant polymers, allowing greater access to the coordinated metal ions because imprinted resins have a relatively low amount of functionalization and are primarily nonionic matrices. The covalent bond that is cleaved to release the taggant molecule can optionally provide an additional polar or ionic site for design and imprinting of the imprint molecule. In preferred embodiments wherein the taggant is associated with the lanthanide in a non-covalent manner, the non-covalently bound taggant is simply leached or washed out after polymerization. For example, for organophosphorus compound imprinted resins, about 1 N aqueous acidic solution may be mixed into the acetone washes, with increasing aqueous acidic phase in each sequential wash, to remove the taggant molecule from the cavities. In certain preferred embodiments, an acidic solvent having a pH of about 4.5 or less is used. In certain other preferred embodiments, resin mass action is used to replace a target anion with an easily exchangeable anion by immersing the polymer in a solution containing the easily exchangeable anion at a suitable pH.

Figure 5:
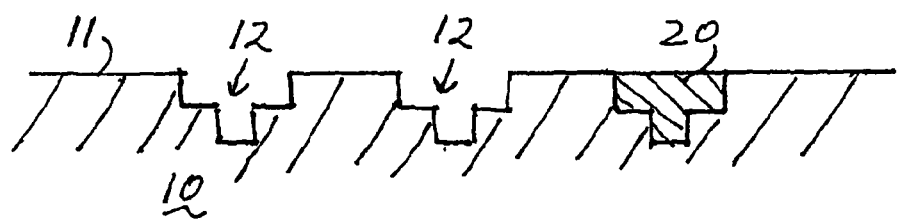

Next, as shown in FIG. 5 the mask is removed leaving a bare surface 11. The areas from which the taggant has been removed will receive and bind the indicator molecules. The indicator molecules will not attach to the previously masked areas on the surface of the MIP body in which the taggant has not been removed.

Figure 6:
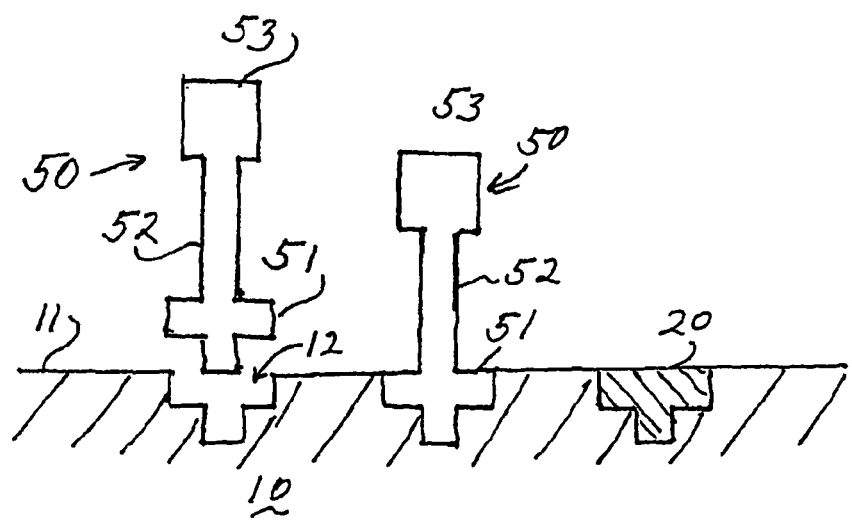

Finally, as shown in FIG. 6, to carry out the identification step, the surface 11 of the body is exposed to a fluid containing the indicator molecules 50. The indicator molecules each include a taggant moiety 51 at one end of the indicator molecule. The taggant moiety has the same general structure as the taggant used as the imprint molecule for creating the MIP except that it is attached to a molecular chain 52, such as a long chain alkyl group, to connect to a marking functional group 53. The marking functional group is any type group having a property which renders the molecule detectible with or without specialized equipment so as to render the marked portion of the MIP body perceptible. Preferably, the marking functional group is a chromophore. For example, a taggant imprint molecule can be an organophosphorus compound such as dimethyl hydrogen phosphate, $(CH_3O)_2P(O)H$. The indicator molecule can have the structure $(CH_3O)_2P(O)$—$(CH_2)_n$—Z wherein Z is a chromophore and —$CH_2$— is an alkylene group wherein n can be a number from 2 to 24. One skilled in the art can synthesize an indicator molecule employing standard laboratory techniques and equipment.

A chromophore is a portion of a molecule which is responsible for electron transitions which result in highly colored or luminescent compounds. Luminescent compounds can be, for example, fluorescent compounds, and will luminesce when illuminated with ultraviolet light or infrared light when exposed to a light source, e.g., a lamp or light emitting diode of the correct wavelength. Groups such as —$NO_2$, C═O, —N═N—, C═N, C═S, and N═O, are typical of chromophores. Various chromophoric compounds include, but are not limited to, 5,10,15,20-tetrakis-(1-methyl-4-pyridyl) 21H, 23H-porphine, tetra-p-tosylate salt, available from Aldrich CbLemical Corporation, 5,10,15,20-tetrakis-(1-methyl-4-pyridyl)-21H,23H-porphine, tetra-chloride salt, 5,10,15,20-tetrakis-(1-methyl-4-pyridyl)-21H,23H-porphine, tetra-bromide salt, 5,10,15,20-tetrakis-(1-methyl-4-pyridyl)-21H, 23H-porphine, tetra-acetate salt, 5,10,15,20-tetrakis-(1-methyl-4-pyridyl)-21H,23H-porphine, tetra-perchlorate salt, 5,10,15,20-tetrakis-(1-methyl-4-pyridyl)-21H,23H-porphine, tetra-fluoroborate salt, 5,10,15,20-tetrakis-(1-methyl-4-pyridyl)-21H,23H-porphine, tetra-perchlorate salt, 5,10, 15,20-tetrakis-(1-methyl-4-pyridyl)-21H,23H-porphine, tetra-triflate salt, 5,10,15,20-tetralds-(1-hydroxymethyl-4-pyridyl)-21H,23H-porphine, tetra-p-tosylate salt, 5,10,15, 20-tetrakis-[1-(2-hydroxyethyl)-4-pyridyl]-21H,23H-porphine, tetra-chloride salt, prepared as described, for example, by V. N. Madakyan, Chemistry of Heterocyclic Compounds, 1986, pages 167 to 171, 5,10,15,20-tetrakis-[1-(3-hydroxypropyl)-4-pyridyl]-21H,23H-porphine, tetra-p-tosylate salt, 5,10,15,20-tetrakis-[1(2-hydroxypropyl)-4-pyridyl]-21H, 23H-porphine, tetra-p-tosylate salt, 5,10,15,20-tetrakis-[1-(2-hydroxyethoxyethyl)-4-pyridyl]-21H,23H-porphine, tetra-p-tosylate salt, 5,10,15,20-tetrakis-[1-(2-hydroxyethoxypropyl)-4-pyridyl]-21H,23H-porphine, tetra-p-tosylate salt, 5,10,15,20-tetrakis-[4-(trimethylammonio)phenyl]-21H,23H-porphine, tetra-p-tosylate salt, available from Aldrich Chemical Corporation, 5,10,15,20-tetrakis-[4-(trimethylammonio)phenyl]-21H,23H-porphine, tetra-chloride salt, 5,10,15,20-tetrakis-[4-(trimethylammonio)phenyl]-21H,23H-porphine, tetra-bromide salt, 5,10,15,20-tetrakis-[4-(trimethylammonio)phenyl]-21H,23H-porphine, tetra-acetate salt, 5,10,15,20-tetrakis-[4-(trimethylaminonio) phenyl]-21H,23H-porphine, tetra-perchlorate salt, 5,10,15, 20-tetrakis-[4-(trimethylammonio)phenyl]-21H,23H-porphine, tetra-fluoroborate salt, 5,10,15,20-tetrakis-[4-(trimethylammonio)phenyl]-21H,23H-porphine, tetra-triflate salt, meso-(N-methyl-X-pyridinium)$_n$-(phenyl) 4-n-21H,23H-porphine, tetra-p-tosylate salt, where n is an integer of value 0, 1, 2, or 3, and where X=4-(para), 3-(meta), or 2-(ortho) refers to the position of the nitrogen in the pyridinium substituent, prepared as described, for example, by M. A. Sari et al. in Biochemistry, 1990, 29, 4205 to 4215; meso-tetrakis-[o-(N-methylnicotinamido)phenyl]-21H,23H-porphine, tetra-methyl sulfonate salt, prepared as described, for example, by G. M. Miskelly et al. in Inorganic Chemistry, 1988, 27, 3773 to 3781; 5,10,15,20-tetrakis-(2-sulfonatoethyl-4-pyridyl)-21H,23H-porphine, chloride salt, prepared as described by S. Igarashi and T. Yotsuyanagi in Chemistry Letters, 1984, 1871; 5,10,15,20-tetrakis-(carboxymethyl-4-pyridyl)-21H,23H-porphine, chloride salt, 5,10,15,20-tetrakis-(carboxyethyl-4-pyridyl)-21H,23H-porphine, chloride salt, 5,10,15,20-tetrakis-(carboxyethyl-4-pyridyl)-21H,23H-porphine, bromide salt, 5,10,15,20-tetrakis-(carboxylate-4-pyridyl)-21H,23H-porphine, bromide salt, prepared as described by D. P. Arnold in Australian Journal of Chemistry, 1989, 42, 2265 to 2274; 2,3,7,8,12,13,17,18-octa-(2-hydroxyethyl)-21H-23H-porphine, 2,3,7,8,12,13,17,18-octa-(2-hydroxyethoxyethyl)-21H-23H-porphine, 2,3,7,8,12,13, 17,18-octa-(2-aminoethyl)-21H-23H-porphine, 2,3,7,8,12, 13,17,18-octa-(2-hydroxyethoxypropyl)-21H-23H-porphine, mixtures thereof, and the like. These dyes are available from various sources, and also many of them can be prepared by known means, such as by following the general synthesis described in Organic Synthesis, A. I. Meyers, Editor, Volume 70, 68 to 72 (1991) and the references included therein, the disclosures of which are totally incorporated herein by reference.

The chromophore can render the indicator molecule visibly colored under standard ambient lighting conditions. Alternatively, it can be fluorescent, responding to specific wavelengths of light to render the indicator molecule visible when illuminated by specialized equipment such as ultraviolet lamps.

The indicator molecules can be incorporated into a solution which is applied to the MIP body by any suitable means such as spraying, wiping, dipping the body into the solution, etc. The excess solution is wiped off and any color or pattern made visible identifies the body 10. In the selected unmasked areas the taggant moiety of the indicator moles will engage the molecular cavities 12 attaching the indicator molecules so as to mark the selected areas. In the masked areas the indicator molecules will not attach themselves to the surface 11 of the body because the molecular cavities are already occupied with the taggant molecules. The indicator molecules can then be detected visually or by other means, with or without the use of instrumentation.

In the following examples, Processable Molecularly Imprinted Polymers (MIPs) were prepared by Reversible Addition Fragmentation Chain Transfer (RAFT) polymerization followed by Ring Closing Metathesis (RCM) to generate the processable MIP. The polymer's core consisted of a dithiobenzoate substituted tri(β-diketonate) europium (III) complex. The β-diketonate was the anion of (dithiobenzoic acid 1-[4-(4,4,4-trifluoro-butane-1,3-dione)-naphthalen-1-yl]-ethyl ester (HDBNTFA). HDBNTFA was prepared by the condensation of dithiobenzoic acid with 4,4,4-trifluoro-1-(4-vinyl-naphthalen-1-yl)-butane-1,3-dione in carbon tetrachloride. The tris DBNTFA europium complex served as a polymerization substrate for three armed RAFT mediated polymers. The arms were AB block copolymers where block A was 1-but-3-enyl-4-vinylbenzene and block B was styrene. The but-3-enyls of block A were reacted by RCM with $2^{nd}$ generation Grubb's catalyst to give an intramolecularly crosslinked core. The intramolecularly crosslinked MIP was soluble in common organic solvents and had a molecular weight of approximately 50,000 atomic mass units (amu) and a molecular weight distribution (MWD) of about 1.3.

All reactions and manipulations were carried out under an argon atmosphere using standard Schlenk line techniques. Dry solvents, when needed, were distilled from either Na/benzophenone (aromatics and ethers), or $CaH_2$ (halogenated and nonhalogenated hydrocarbons).

NMR was performed on either a Bruker AC-200 MHz spectrometer or an Anasazi 90 MHz spectrometer; FT-IR was performed on a Bomems MB-122; GC/MS was performed on a Shimadzu QP 5050A. Molecular weight data was determined by a Varian Prostar Model 430 BPLC equipped with a Polymer Laboratories PLgel 5 um MiniMix C, 250×4.6 mm column. The HPLC was calibrated with Polystyrene cal kit S-M-10 and Galaxy Software's GPC Module performed the related calculations.

All chemicals were provided by Sigma-Aldrich or Strem unless otherwise stated, and were used without further purification. Vinyl naphthoyl trifluoroacetone (VNTFA) and 1-but-3-enyl-4-vinylbenzene were synthesized by previously published methods. Dithiobenzoic acid was synthesized by means found by Rizzardo et al.

A flow chart of the synthesis procedure as illustrated in Examples 1-5 is presented in FIG. 1.

EXAMPLE 1

This example illustrates the synthesis of the ligand, (Dithiobenzoic acid 1-[4-(4,4,4-trifluoro-butane-1,3-dione)-naphthalen-1-yl]-ethyl ester (HDBNTFA). Vinyl naphthoyl trifluoroacetone (2.92 g, 10 mmol), dithiobenzoic acid (1.54 g, 10 mmol), and carbon tetrachloride (6 mL) were placed together into a 15 mL roundbottomed flask equipped with a reflux condenser under an argon atmosphere. The reaction was heated to 70° C. for 16 hours when a $2^{nd}$ aliquot of dithiobenzoic acid (0.77 g, 5 mmol) and the reaction was continued for another 4 hours. The solvent was removed by vacuum and the final product was isolated by column chromatography through silica gel with 60/40 hexanes/chloroform as eluent to give a viscous red oil (2.2 g, 50% yield).

EXAMPLE 2

This example illustrates the synthesis of the europium complex, $(DBNTFA)_3Eu.xH_2O$. HDBNTFA (1.0 g, 2.24 mmol) synthesized in Example 1 was dissolved in THF (5 mL) in a 15 mL roundbottomed flask and 1.0 M sodium hydroxide (2.46 mL) was added dropwise. A solution of europium chloride hexahydrate (0.274 g, 0.75 mmol) in water (2 mL) was added and the flask was equipped with a reflux condenser. The reaction was heated to reflux for 3 hours before excess methanol was added to end the reaction. The precipitate were remnoved by filtration, dried, dissolved in ether, filtered again, and precipitated into hexanes. The precipitate was isolated by filtration, which gave a red solid (750 mg, 66% yield).

EXAMPLE 3

This example illustrates the reaction of the europium complex with the target analyte (dimethyl hydrogen phosphate) and a monomer to provide an MIP, i.e., $(DBNTFA)_3Eu.2(CH_3O)2P(O)H$-tris(poly-1-but-3-enyl-4-vinybenzene). $(DBNTFA)_3Eu.xH_2O$ (40 mg, 26 µmol), 1-but-3-enyl-4-vinylbenzene (880 mg, 5.62 mmol), dimethylhydrogen phosphate (6 mg, 52 µmol), and 2,2'-azobis(2,4-dimethyl valeronitrile) (1.5 mg, 6 µmol) were placed into a reaction flask and the flask was subjected to 3 freeze/pump/thaw cycles. The flask was left under an argon atmosphere and was heated to 50° C. for 7 hours when the excess 1-but-3-enyl-4-vinylbenzene was removed by vacuum.

EXAMPLE 4

This example illustrates the preparation of a block copolymer $(DBNTFA)_3Eu. 2(CH_3O)_2P(O)H$-tris(poly-1-but-3-enyl-4-vinylbenzene-block-polystyrene). Styrene (1.56 g, 15 mmol) was added to the reaction flask from the preceding reaction. The flask was subjected to 3 freeze/pump/thaw cycles, and was heated to 100° C. for 72 hours before the excess styrene was removed by vacuum.

EXAMPLE 5

This example illustrates the preparation of $(DBNTFA)_3Eu. 2(CH_3O)_2P(O)H$-tris(poly-1-but-3-enyl-4-vinylbenzene-block-polystyrene)-crosslinked. $(DBNTFA)_3Eu. 2(CH_3O)_2P(O)H$-tris(poly-1-but-3-enyl-4-vinylbenzene-block polystyrene) (500 mg) and ruthenium catalyst (50 mg, 59 µmol) were placed in at 250 mL Schlenk flask. The flask was evacuated and backfilled 3 times with argon. Methylene chloride (150 mL) was added and the solution was heated to reflux for 18 hours and then room temperature for an additional 6 hours. The solution was filtered through silica gel, the solution concentrated, and the crosslinked polymer precipitated by addition to methanol. A white powder (355 mg) was collected.

EXAMPLE 6

This example illustrates RAFT polymerization of $L_3Eu$-PMP with methacrylate wherein L is DBNTFA, dithiobenzoic acid 1-[4-(4,4,4-trifluoro-butane-1,3-dione)-naphthalen-1-yl]-ethyl ester.

16 Mmol of ethylene glycol dimethacrylate, 8 mmol methylmethacrylate, 4 mL toluene solvent, 0.44 mmol 2,2'-azobis-(2,4-dimethylvaleronitrile) which is available as Waco V-65 initiator, 0.029 mmol PMP and $L_3Eu$ were placed in a disposable glass reaction flash equipped with a stir bar. The solution was subjected to three freeze/pump/thaw cycles with argon backfill. The solution was placed into an oil bath heated to 60° C. for 18 hours before the solvent and unreacted monomer were removed by healing to 60° C. under vacuum (0.5 torr) for 4 hours. The resulting salmon-colored polymer was ground with a freezer mill to a fine powder.

EXAMPLE 7

Essentially the same procedure as Example 6 was conducted except that the monomers used were 22 mmol divinylbenzene and 11 moles styrene. The resulting salmon-colored powder was ground in a freezer mill to a fine powder.

EXAMPLE 8

The MIP resulting from Example 6 was cleaned by solvent extraction with isopropanol to remove PMP. The isopropanol was tested for any leached europium and was found to have none, thus showing that the complex is fully incorporated into the polymer and europium does not wash out.

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

What is claimed is:

1. A method for identifying a product comprising:
a) providing a solid body fabricated from at least a molecularly imprinted polymer having molecular sized cavities adapted to selectively receive and bind molecules having a specific taggant molecular structure, said molecular sized cavities being disposed on at least a portion of an exterior surface of the body; and,
b) applying to the surface of the body a composition containing indicator molecules having a taggant moiety at one end having the taggant molecular structure and a marking functional group tethered to the taggant moiety by a molecular chain, said taggant moieties engaging and binding to the molecular sized cavities so as to mark the portion of the surface of the body with the indicator molecules bound thereto, said marking functional groups rendering the marked portion of the surface perceptible with or without detection instrumentation;
wherein the molecularly imprinted polymer is made in accordance with the steps of:
(a) providing a complex comprising a compound of the general formula $L_3M$ wherein L is the same or different and is a β-diketone ligand containing the same or different chain transfer moiety and M is a lanthanide element;
(b) reacting the complex with a target analyte to provide an adduct containing the target analyte;
(c) co-polymerizing the adduct with a monomer and cross-linking agent to provide a polymer; and,
(d) removing the target analyte from the polymer to provide the molecularly imprinted polymer.

2. The method of claim 1, wherein the lanthanide element M is selected from the group consisting of lanthanum, cerium, praseodymium, neodymium, promethium, samarium, europium, gadolinium, terbium, dysprosium, holmium, erbium, thulium, ytterbium, and lutetium.

3. The method of claim 1, wherein the ligands $L_3$ are each the same ligand.

4. The method of claim 1, wherein the β-diketone ligands have the structure:

$R^1$—C(O)—$CR^2_2$—C(O)—$R^3$ wherein $R^1$ is a hydrocarbon group having 1 to about 20 carbons containing a chain transfer moiety; $R^2$ can be the same or different and is hydrogen or a hydrocarbon group having from 1 to about 12 carbon atoms and $R^3$ is a straight or branched chain alkyl group of 1 to about 12 carbon atoms optionally containing one or more halogen atoms.

5. The method of claim 4, wherein $R^3$ is an alkyl halide.

6. The method of claim 5, wherein the alkyl halide is —$CF_3$.

7. A method for identifying a product comprising:
a) providing a solid body fabricated from at least a molecularly imprinted polymer having molecular sized cavities adapted to selectively receive and bind molecules having a specific taggant molecular structure, said molecular sized cavities being disposed on at least a portion of an exterior surface of the body; and,
b) applying to the surface of the body a composition containing indicator molecules having a taggant moiety at one end having the taggant molecular structure and a marking functional group tethered to the taggant moiety by a molecular chain, said taggant moieties engaging and binding to the molecular sized cavities so as to mark the portion of the surface of the body with the indicator molecules bound thereto, said marking functional groups rendering the marked portion of the surface perceptible with or without detection instrumentation;
wherein the chain transfer moiety is selected from the group consisting of dithiocarboxylic ester, trithiocarbonate and benzyl iodide.

8. The method of claim 7, wherein the dithiocarboxylic ester is of the general formula —S—C(S)R wherein R is a hydrocarbon group having from 1 to about 20 carbon atoms.

9. A method for identifying a product comprising:
a) providing a solid body fabricated from at least a molecularly imprinted polymer having molecular sized cavities adapted to selectively receive and bind molecules having a specific taggant molecular structure, said molecular sized cavities being disposed on at least a portion of an exterior surface of the body; and,
b) applying to the surface of the body a composition containing indicator molecules having a taggant moiety at one end having the taggant molecular structure and a marking functional group tethered to the taggant moiety by a molecular chain, said taggant moieties engaging and binding to the molecular sized cavities so as to mark the portion of the surface of the body with the indicator molecules bound thereto, said marking functional groups rendering the marked portion of the surface perceptible with or without detection instrumentation;
wherein the molecular sized cavities are provided on selected portion(s) of the exterior surface of the body in accordance with the following steps:
providing a solid body fabricated from molecularly imprinted polymer having taggant molecules complexed therein;
covering predetermined areas(s) of the surface of the body with a mask to provide unmasked portion(s) of selected size and configuration;
removing the taggant molecules from the selected unmasked portion(s); and,
removing the mask from the surface of the body.

10. The method of claim 9, wherein the polymer is an epoxy resin.

11. The method of claim 9, wherein the marking functional group is a chromophore.

12. The method of claim 11, wherein the chromophore is visibly colored.

13. The method of claim 11, wherein the chromophore luminesces when illuminated with ultraviolet light or infrared light.

14. The method of claim 9, wherein the molecular chain comprises an alkylene group having the formula —$(CH_2)_n$— wherein n is an integer of from 2 to about 24.

15. The method of claim 9, wherein the selected unmasked portion(s) are configured as information conveying indicia.

16. The method of claim 9, further comprising the step of removing the composition containing the indicator molecules from the surface of the body, leaving the indicator molecules bound to and marking the selected portion(s) of the surface from which the taggant molecules have been removed, but not bound to the previously masked areas.

17. A product identification system comprising:
a) a package body fabricated from at least a molecularly imprinted polymer having molecular sized cavities adapted to selectively receive and bind molecules having a specific taggant molecular structure, said molecular sized cavities being disposed on selected portions of an exterior surface of the body, said selected portions being configured in the form of information conveying indicia; and, b) a developing composition for developing the selected portions as an image, said developing composition including indicator molecules having a taggant moiety at one end having the taggant molecular structure and a marking functional group tethered to the taggant moiety by a molecular chain, said taggant moieties engaging and binding to the molecular sized cavities so as to mark the portion of the surface of the body with the indicator molecules bound thereto, said marking functional groups rendering the marked portion of the surface perceptible with or without detection instrumentation;

wherein the molecular sized cavities are provided on selected portion(s) of the exterior surface of the body in accordance with the following steps:

providing a solid body fabricated from molecularly imprinted polymer having taggant molecules complexed therein;

covering predetermined areas(s) of the surface of the body with a mask to provide unmasked portion(s) of selected size and configuration;

removing the taggant molecules from the selected unmasked portion(s); and removing the mask from the surface of the body.

18. The system of claim 17, wherein the polymer is an epoxy resin.

19. The system of claim 17, wherein the marking functional group is a chromophore.

20. The system of claim 19, wherein the chromophore is visibly colored.

21. The system of claim 19, wherein the chromophore luminesces when illuminated with ultraviolet light or infrared light and the system includes a light source.

22. The system of claim 17, wherein the molecular chain comprises an alkylene group having the formula —$(CH_2)_n$— wherein n is an integer of from 2 to about 24.

23. A product identification system comprising:

a) a package body fabricated from at least a molecularly imprinted polymer having molecular sized cavities adapted to selectively receive and bind molecules having a specific taggant molecular structure, said molecular sized cavities being disposed on selected portions of an exterior surface of the body, said selected portions being configured in the form of information conveying indicia; and, b) a developing composition for developing the selected portions as an image, said developing composition including indicator molecules having a taggant moiety at one end having the taggant molecular structure and a marking functional group tethered to the taggant moiety by a molecular chain, said taggant moieties engaging and binding to the molecular sized cavities so as to mark the portion of the surface of the body with the indicator molecules bound thereto, said marking functional groups rendering the marked portion of the surface perceptible with or without detection instrumentation;

wherein the molecularly imprinted polymer is made in accordance with the steps of (a) providing a complex comprising a compound of the general formula $L_3M$ wherein L is the same or different and is a β-diketone ligand containing the same or different chain transfer moiety and M is a lanthanide element;

(b) reacting the complex with a target analyte to provide an adduct containing the target analyte;

(c) co-polymerizing the adduct with a monomer and cross-linking agent to provide a polymer; and, (d) removing the target analyte from the polymer to provide the molecularly imprinted polymer.

24. The system of claim 23, wherein the lanthanide element M is selected from the group consisting of lanthanum, cerium, praseodymium, neodymium, promethium, samarium, europium, gadolinium, terbium, dysprosium, holmium, erbium, thulium, ytterbium, and lutetium.

25. The system of claim 23, wherein the ligands $L_3$ are each the same ligand.

26. The system of claim 23, wherein the β-diketone ligands have the structure:

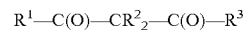

$$R^1-C(O)-CR^2_2-C(O)-R^3$$

wherein $R^1$ is a hydrocarbon group having 1 to about 20 carbons containing a chain transfer moiety; $R^2$ can be the same or different and is hydrogen or a hydrocarbon group having from 1 to about 12 carbon atoms and $R^3$ is a straight or branched chain alkyl group of 1 to about 12 carbon atoms optionally containing one or more halogen atoms.

27. The system of claim 26, wherein $R^3$ is an alkyl halide.

28. The system of claim 27, wherein the alkyl halide is —$CF_3$.

29. The system of claim 23, wherein the chain transfer moiety is selected from the group consisting of dithiocarboxylic ester, trithiocarbonate and benzyl iodide.

30. The system of claim 29, wherein the dithiocarboxylic ester is of the general formula —S—C(S)R wherein R is a hydrocarbon group having from 1 to about 20 carbon atoms.

* * * * *